(12) United States Patent
Garris et al.

(10) Patent No.: US 8,771,212 B1
(45) Date of Patent: Jul. 8, 2014

(54) ADJUSTABLE SPLINT

(76) Inventors: Edward D. Garris, Charlottesville, VA (US); Brett W. Shimel, Charlottesville, VA (US)

(*) Notice: Subject to any disclaimer, the term of this patent is extended or adjusted under 35 U.S.C. 154(b) by 1760 days.

(21) Appl. No.: 11/156,791

(22) Filed: Jun. 20, 2005

Related U.S. Application Data

(60) Provisional application No. 60/581,576, filed on Jun. 21, 2004.

(51) Int. Cl.
*A61F 5/00* (2006.01)

(52) U.S. Cl.
USPC .............................. 602/20; 602/22

(58) Field of Classification Search
USPC .............. 602/5–7, 20–22; 128/878–880, 893, 128/894
See application file for complete search history.

(56) References Cited

U.S. PATENT DOCUMENTS

| | | | |
|---|---|---|---|
| 2,423,538 A | 7/1947 | Whiteford | |
| 2,548,378 A | 4/1951 | Kleinfeld | |
| 3,170,460 A | 2/1965 | Stilson | |
| 4,103,682 A | 8/1978 | Franzl | |
| 4,243,026 A | 1/1981 | Barber | |
| 4,270,528 A | 6/1981 | Hanson | |
| 4,297,992 A | 11/1981 | LaRue | |
| 4,441,489 A | 4/1984 | Evans | |
| 4,665,907 A | 5/1987 | Leverette | |
| 4,674,487 A | 6/1987 | Schaeffer | |
| 4,770,166 A | 9/1988 | Garris | |
| 4,817,488 A * | 4/1989 | de los Santos | 84/319 |
| 4,932,396 A | 6/1990 | Garris | |
| 5,520,626 A | 5/1996 | Schaeffer | |
| 5,971,945 A | 10/1999 | Garris | |
| 5,991,918 A | 11/1999 | Choate | |
| 6,110,136 A * | 8/2000 | Belkin | 602/22 |
| 6,904,916 B2 * | 6/2005 | Bakane | 128/885 |
| 6,932,782 B2 * | 8/2005 | Ferraioli | 602/22 |
| 2004/0002673 A1 | 1/2004 | Ferraioli | |

\* cited by examiner

*Primary Examiner* — Michael A. Brown
(74) *Attorney, Agent, or Firm* — Michael Haynes PLC; Michael N. Haynes

(57) ABSTRACT

Certain exemplary embodiments can comprise a splint for a body part, such as a human digit. The splint can include a unitary, semi-rigid, arcuate, and/or toroidal member; a first lock portion integral to the member; and a second lock portion integral to the member. The first lock portion can be adapted to releasably lockably engage the second lock portion so as to allow for continuously and/or incrementally adjustable contact of at least a portion of the member with a predetermined portion of the body part of a wearer of the splint.

30 Claims, 9 Drawing Sheets

ADJUSTABLE SPLINT

CROSS-REFERENCES TO RELATED APPLICATIONS

This application claims priority to, and incorporates by reference herein in its entirety, pending U.S. Provisional Patent Application Ser. No. 60/581,576, filed 21 Jun. 2004.

BRIEF DESCRIPTION OF THE DRAWINGS

A wide variety of potential embodiments will be more readily understood through the following detailed description of certain exemplary embodiments, with reference to the accompanying exemplary drawings in which.

DEFINITIONS

Figure 1:
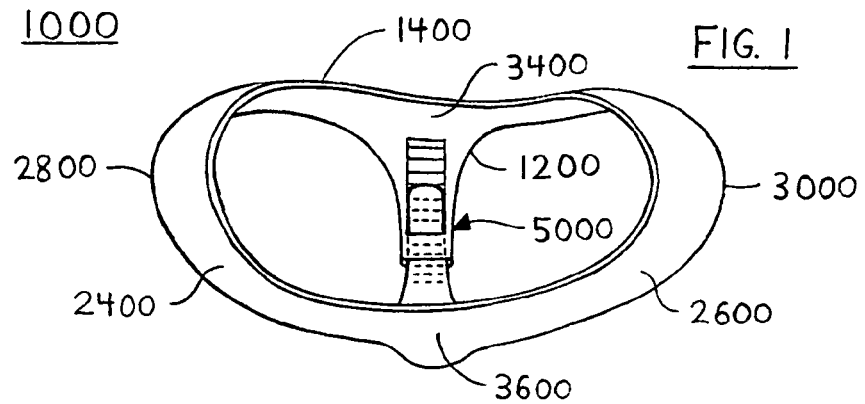
FIG. 1 is a perspective view of an exemplary embodiment of a finger splint 1000.

When the following terms are used herein, the accompanying definitions apply:

a—at least one.
acute—less than 90 degrees.
adapted to—made suitable or fit for a specific use or situation.
adapter—a device used to effect operative compatibility between different parts of one or more pieces of an apparatus or system.
adjustable—configured to change, match, and/or fit.
annular—shaped like a ring.
apparatus—an appliance or device for a particular purpose
arcuate—curved, bent, and/or having the form of a bow.
arcuate semi-elliptical—having the form or shape of a half of a ellipse, that half curved so that the semi-ellipse is not planar.
arcuate toroidal—having the form or shape of a half of a toroid that is curved so that the toroid is not planar, e.g., resembling a donut that has been bent partially around an axis substantially and/or nearly parallel to an axis of the donut, yet outside the major plane of the donut.
axis—a straight line with respect to which the different parts of a magnitude are symmetrically arranged; as, the axis of a cylinder, i.e., the axis of a cone, that is, the straight line joining the vertex and the center of the base; the axis of a circle, any straight line passing through the center.
below—beneath; in a lower place.
body—a main and/or central part.
body facing—oriented toward and/or touching the skin.
can—is capable of, in at least some embodiments.
channel—a groove.
circumscribe—to draw a geometric figure around another figure so that the two are in contact but do not intersect.
communicating—connected.
comprising—including but not limited to.
connect—to join or fasten together.
contact—coming together in immediate proximity and/or touching.
coupleable—capable of being joined, connected, and/or linked together.
coupling—linking in some fashion.
cross-section—a section formed by a plane cutting through an object at a right angle to an axis.
define—to establish the outline, form, or structure of
deflectable—configured to bend and/or deviate.
digit—any of the divisions (such as a finger or toe) in which the limbs of amphibians and all higher vertebrates including humans terminate, which are typically five in number but may be reduced (as in the horse), and which typically have a series of phalanges bearing a nail, claw, or hoof at the tip.
disposed—placed, arranged, and/or oriented.
distal—farther to a point of reference, such as a portion of an extended hand that is further from the face.
dorsal—of, toward, on, in and/or near the back of a part or body.
dovetail—a fan-shaped tenon that forms a tight interlocking joint when fitted into a corresponding mortise.
egress—a place of exiting; v. to exit.
elongated—drawn out, made spatially longer, and/or having more length than width.
end—an extremity of something that has length; a terminus.
engage—to mesh, mate, and/or connect.
engageable—configured to mesh, mate, and/or connect
environment facing—oriented away from the skin.
formed—constructed.
guide member—a part that directs.
human body—the physical part of a person.
ingress—a place of entering; v. to enter.
install—to connect or set in position and prepare for use.
integrally—in a complete, built-in manner.
intersecting—meeting at a point.
intersection—a point and/or line defined by the meeting of two or more items.
inwardly—toward the nearest skin of the wearer.
length—the measurement of the extent of something along its greatest dimension.
line—a geometric figure formed by a point moving along a fixed direction and the reverse direction.
lockably—configured to lock.
locking—configured to fix in place, hold, entangle, and/or interlock securely.
longitudinal—of or relating to longitude or length.
major—relatively great in size or extent.

manipulation—manual adjustment.

mating—one of a matched pair.

may—is allowed to, in at least some embodiments.

member—a distinct part of a whole.

method—a process, procedure, and/or collection of related activities for accomplishing something.

minor axis—the shorter or shortest axis of an ellipse or ellipsoid.

mount—to fix and/or attach to securely.

opposing—located opposite, in contrast, and/or in counterbalance.

plane—a surface containing all the straight lines that connect any two points on it.

plurality—the state of being plural and/or more than one.

portion—a section or quantity within a larger thing; a part of a whole.

positioned—to put in place or position.

predetermined—established in advance.

promoting—encouraging and/or contributing to.

proximal—nearer to a point of reference, such as a portion of an extended hand that is nearer the face.

pull-through opening—a breach and/or aperture through which an object can be moved toward a source of an applied force.

radially—in a manner that radiates from and/or converges to a common center.

releasably—configured to release.

removably—configured to be moved from a place or position occupied.

ridge—a long, raised strip.

ring portion—an annular or partially annular member.

ring size—a measurement determined by the diameter of the finger on which a ring will be worn and the knuckle, which the ring must slip over comfortably.

semi-elliptical—having, at least approximately, the form or shape of half of an ellipse.

semi-major axis—one-half the major axis of an ellipse; the distance from the center of an ellipse to one end.

semi-rigid—moderately, but not fully, inflexible or stiff.

separable—configured to be non-destructively set apart, disengaged, and/or disunited.

set—a related plurality.

slideably—configured to o move over a surface while maintaining substantially smooth continuous contact.

splint—a device used to prevent one or more motions of a joint.

strap—a relatively thin band, having an elliptical, rectangular, and/or polygonal cross-section, and used for fastening and/or clamping objects together and/or into position.

substantially—to a great extent or degree.

support—to bear the weight of, especially from below.

surface—the exterior and/or outer boundary of an object.

system—a collection of mechanisms, devices, data, and/or instructions, the collection designed to perform one or more specific functions.

teeth—a series of projecting parts adapted for gripping.

toroid—A surface generated by a closed curve rotating about, but not intersecting or containing, an axis in its own plane.

toroidal—of or relating to or shaped like a toroid.

transverse—situated or lying across; crosswise; at a right angle to a long axis of a body.

unitary—having the nature of a unit; whole; not separated.

upwardly—orthogonal to and opposite a direction faced by an outstretched palm and/or sole, as the case may be.

vertex—the point at which the sides of an angle intersect.

volar—of or relating to the sole of the foot or the palm of the hand.

wall—a layer of material that at least partially encloses space.

width—the extent of something from side to side and/or orthogonal to length.

DETAILED DESCRIPTION

Each of following United States patent documents is incorporated by reference herein in its entirety: U.S. Pat. No. 2,423,538 (Whiteford); U.S. Pat. No. 2,548,378 (Kleinfeld); U.S. Pat. No. 3,170,460 (Stilson); U.S. Pat. No. 4,103,682 (Franzl); U.S. Pat. No. 4,243,026 (Barber); U.S. Pat. No. 4,270,528 (Hanson); U.S. Pat. No. 4,297,992 (LaRue); U.S. Pat. No. 4,441,489 (Evans); U.S. Pat. No. 4,665,907 (Leverette); U.S. Pat. No. 4,674,487 (Schaeffer); U.S. Pat. No. 4,770,166 (Garris); U.S. Pat. No. 4,932,396 (Garris); U.S. Pat. No. 5,520,626 (Schaeffer); U.S. Pat. No. 5,971,945 (Garris); U.S. Pat. No. 5,991,918 (Choate); U.S. Pat. No. 6,110,136 (Belkin); and 2004/0002673 (Ferraioli).

Rheumatoid and osteoarthritis are incurable diseases that affect a large number of individuals to varying degrees. In severe cases, these disease can be both painful and crippling causing, among other problems, instability, abnormal movement and pain in the interphalangeal joints. Similarly, Ehlers-Danlos Syndrome is a disease that, in some forms can cause hypermobility in some, many, and/or all the joints of the body. Likewise, injury can cause joints to need support and splinting assistance to function properly.

Certain exemplary embodiments can relate to orthopedic splint type devices, such as an adjustable splint for the therapeutic treatment of instability and/or hyperextension of the phalanges. As sometimes described herein, a splint can function as a fulcrum, lever arm type device, which can provide three points of pressure to stabilize a joint. The fulcrum of the splint can lie at, under, over or beside the joint being splinted. The proximal and distal ends of the splint can function as the lever arms, which can lie on the digit being splinted and opposite the fulcrum. This arrangement can allow corrective leverage to be applied to the joint. The length, i.e., the distance between the proximal and distal ends of the splint, the positioning of the fulcrum, and/or the diameter can be individually, independently adjustable for proper fit and/or function of the splint.

Certain exemplary embodiments can provide one or more adjustable splints and/or orthopedic support devices that can block and/or prevent fingers and/or other anatomical members from moving in abnormal directions while allowing full, normal range of motion. Discussed herein are certain exemplary embodiments, some of which can provide one or more finger splints that can help block hyperextension and/or hyperflexion and/or alleviate lateral instability of the interphalangeal joints.

As described herein, certain exemplary embodiments can provide adjustable splints that can be custom fit to the digits and/or fingers of individual patients in order to accomplish therapeutic goals. In the case of fingers, by custom fitting splints, all sizes of fingers, thin or fat, short or long, can be properly splinted. The custom fit can be proximal and/or distal to the affected joint and/or can include a splint of correct length and circumference.

Certain exemplary embodiments can provide splints that can adjusted to accommodate periodic changes in the size of, for example, a finger, due to edema associated with injury or disease, thereby potentially eliminating any need for exchanging one splint for another splint of larger or smaller size as indicated by the specific condition.

As shown in some of the attached figures, certain exemplary embodiments can provide an adjustable splint from a single piece of semi-rigid yet deformable material, having a splint body and one or more elongated straps and/or locking members. The straps can connect together in a toothed ratchet manner, to form a continuous semi-circular length of material connected to each other and to the body of the splint. The toothed ratchet portion of the elongated straps can be held at a fixed position, after adjustment, by a releasable latching device.

The adjustable nature of the splint can allow facilities to stock significantly smaller inventories of splints while still providing custom fit splints for their patients. Therefore the hundreds of possible size combinations that might otherwise be required to provide a custom fit splint, when the splint is not adjustable, can be reduced to a small number, such as small, medium, large, and/or extra large individual adjustable splints.

As used herein, words of direction, such as "up", "down", "below", etc., are defined from the perspective of a standing human, the palm and sole of the foot of the human substantially parallel to and facing the ground and/or standing surface of the human.

Described herein is a splint, such as a finger, thumb, wrist, elbow, toe, ankle, and/or knee splint, that can be circumferentially adjustable by a toothed ratchet means to provide a custom fit. An adjustable splint can comprise an arcuate and/or toroidal body comprising two arcuate and/or semi-elliptically shaped ring portions, each such portion comprising approximately half of an ellipse, more or less, such half being defined by approximately bisecting and/or cutting through each ellipse, such as along its approximate minor axis and/or along its approximate major axis, and/or along any other line through the ellipse, the semi-ellipses being joined together at two "intersection points" or "intersections", which can fall along a line. The adjustable splint also can comprise a generally semi-circular adjustable band and/or strap comprising a substantially elliptical, rectangular, and/or closed polygonal cross section and joining the two intersecting points.

The adjustable splint can be made of one or more suitable metals, plastics, and/or other semi-rigid but deformable materials, which can be sufficiently deformable that a person, therapist, and/or patient, can, without tools and/or with the assistance of a very simple tool, adjust the fit of the splint and/or the adjustable band for comfort and/or for changes in size of the splinted body part due to weather, medical, and/or other conditions, etc.

In the case of an adjustable finger splint, as the adjustable strap is tightened, the ring size as measured in a cross-section perpendicular to the longitudinal axis of the finger can effectively decrease and, conversely, as the adjustable strap is loosened, the ring size can effectively increase.

The adjustable finger splint can be slipped over the patient's affected finger(s) and/or positioned such that the adjustable band is directly volar to (under) the interphalangeal joint with the first semi-elliptical ring portion extending distally (forwardly) from the intersection points to the vertex of the first semi-ellipse and the second semi-elliptical ring portion extending proximally (rearwardly) from the intersection points to the vertex of the second semi-ellipse, and further with the intersection points falling on the sides of the affected finger at any point below the dorsal (top-side) surface and/or above the volar (palm-side) surface of the finger.

Alternatively, the positioning of the adjustable finger splint can be rotated such that the adjustable band is directly above (dorsal to) the interphalangeal joint and/or on either lateral side of the interphalangeal joint.

In certain exemplary embodiments, one of several potentially available sizes of adjustable splints can be chosen based on the distance between the vertices of the semi-elliptical rings (and/or based on the overall length of the splint, as measured parallel to a longitudinal axis of the digit) and/or the relation such distance has to the length of the affected finger (or other target body member) and/or the therapeutic goal sought, but with general disregard to the circumference of the affected finger. Once the appropriate length is determined, the semi-circular band can be adjusted to provide a comfortable custom circumferential fit. This custom fit of the splint can maximize and/or optimize the splint's stabilizing effect and/or therapeutic capability.

The adjustable splint can be appropriate for stabilizing and/or either blocking hyperextension or blocking flexion, depending on how it is placed on the digit, of the various joints of the fingers, thumbs, toes, and/or other body parts. As used herein, "joint(s)" refers to the joint(s) being splinted and not to other unaffected joint(s) of the fingers, thumbs, and/or toes, etc. Furthermore, the word "joint(s)" encompasses the thumb interphalangeal (IP) joint and the proximal interphalangeal (PIP) and distal interphalangeal (DIP) joint(s) of the finger(s). The terms "proximal", "distal", "dorsal", "volar", "medial", and "lateral" are well known to those of ordinary skill in the medical devices field.

For purposes of illustration only, the index finger is used to illustrate certain exemplary embodiments, and in particular the PIP of the index finger, which is the articulating joint located between the proximal phalanx and the middle phalanx of the index finger.

The adjustable semi-elliptical splint can be comprised of a splint body and a splint base. The splint body can be comprised of at least two arcuate semi-elliptically shaped bands that can be connected to each other, such as at the ends of, and/or where each pseudo-parent ellipse can be visualized as bisected by, their approximate minor axes. The points of connection, which can be considered the "intersection points" and/or "intersections", can intersect at an angle to form a "V". The angle between the sides of the "V" can be varied according to therapeutic need. The splint base, which can be integrally formed with the splint body, can extend from the intersection points and/or can be comprised of one, two, or more integral, separable, slideably mounted, deflectable, flexible, semi-rigid, elongate, interlocking, and/or cooperating lock members, such as straps, which can have substantially elliptical, rectangular, and/or closed polygonal cross-sections.

The lock members and/or straps can cooperate and releasably interlock to form a single adjustable splint retaining member or base. Each of the individual lock members, straps, and/or the base they form can define an environment-facing surface and/or a body-facing and/or skin-contact surface. The body-facing surface of the one or more individual lock members, straps, and/or the base can provide a substantially flush and/or smooth surface to avoid irritation of the skin and/or body. The environment-facing surface can provide a substantially flush and/or smooth surface to avoid irritating adjacent digits, snagging clothing, etc.

Thus, certain exemplary embodiments can comprise a splint for a body part, such as a human digit. The splint can include a unitary semi-rigid arcuate toroidal member; a first lock portion integral to the arcuate toroidal member; and a second lock portion integral to the arcuate toroidal member.

The first lock portion can be adapted to releasably lockably engage the second lock portion so as to allow for continuously and/or incrementally adjustable contact of at least a portion of the arcuate toroidal member with a predetermined portion of the body part of a wearer of the splint.

Figure 2:
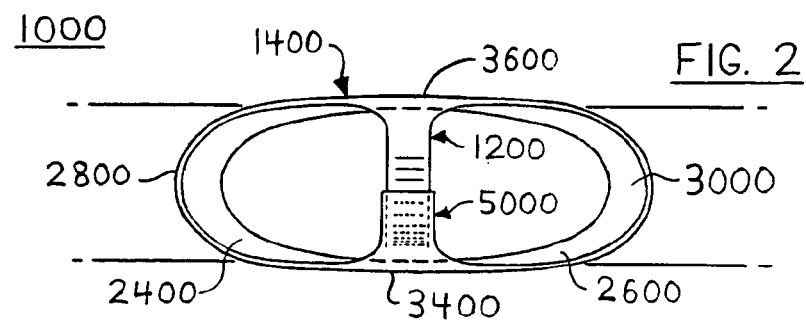
FIG. 2 is a bottom view of an exemplary embodiment of a finger splint 1000.
Figure 3:
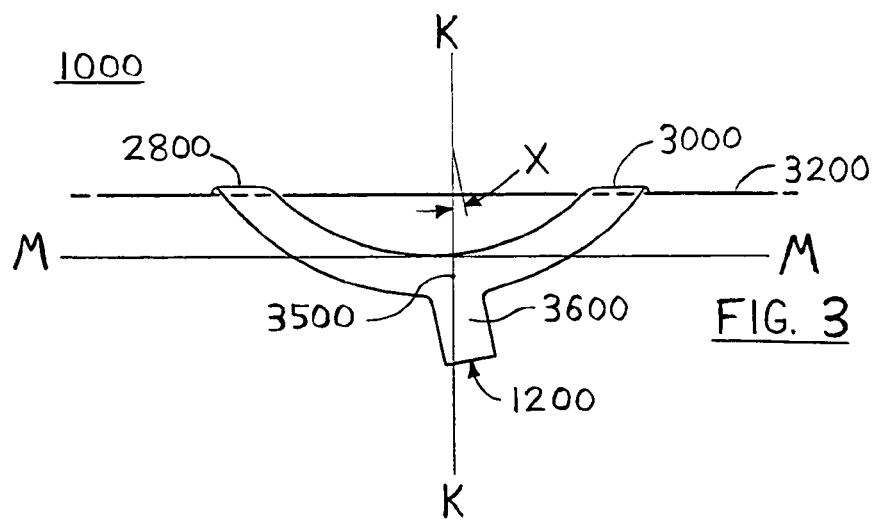
FIG. 3 is a side view of an exemplary embodiment of a finger splint 1000.
Figure 4:
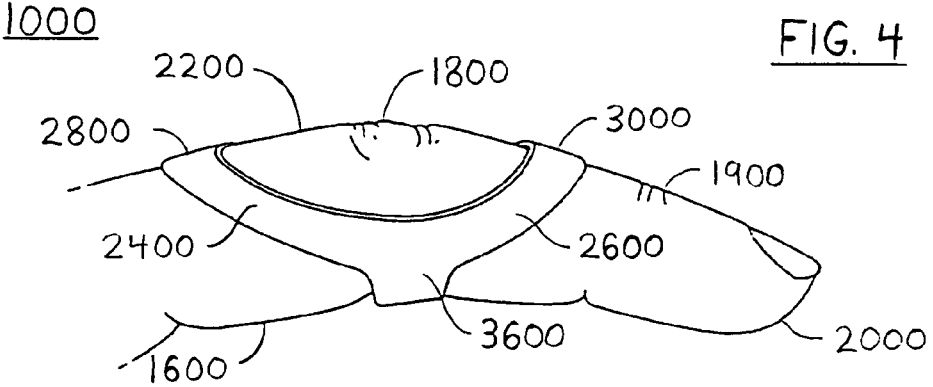
FIG. 4 is a side view of an exemplary embodiment of a finger splint 1000 in position on an extended finger.

With reference now to FIGS. 1-6, shown are one or more exemplary embodiments of one or more systems, devices, and/or digit splints 1000. FIG. 4 is a side view of an exemplary embodiment of splint 1000 on an extended finger. Splint 1000 can block hyperextension of an interphalangeal joint of a finger of a user and/or wearer while allowing full range of motion at an interphalangeal joint as a finger of a user bends into flexion towards the palm of a hand. Splint 1000 can comprise an arcuate angularly inclined base 1200 and an arcuate toroidal member 1400 formed integrally therewith and extending upwardly and radially outwardly therefrom. Base 1200 can be positionable on the volar surface 1600 of an interphalangeal joint 1800 of a finger 2000 of a user. Arcuate toroidal member 1400 can be positionable on the dorsum 2200 of a finger 2000 of a user. Arcuate toroidal member 1400 can be angularly inclined to conform to the dorsum 2200 of a finger 2000 of a user when a finger 2000 is in an extended position without hyperextension.

Figure 6:
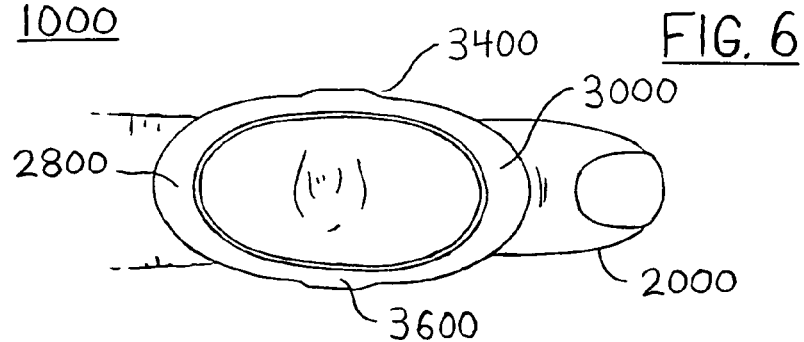
FIG. 6 is a top view of an exemplary embodiment of a finger splint 1000 on an extended finger.

As shown in FIGS. 1, 2 and 6, arcuate toroidal member 1400 can have a pair of opposed substantially semi-elliptical shaped portions, defined herein as the proximal portion 2400 and the distal portion 2600. Each of the pair of opposed substantially semi-elliptical shaped portions can have a bight section 2800 and 3000 respectively, which can include the respective vertex of the corresponding substantially semi-elliptical shaped portion, and/or which in normal use, can resist hyperextension of the digit. Arcuate toroidal member 1400 can be angularly inclined with respect to the mid-longitudinal axis of an extended finger 2000 to conform to the dorsum 2200 of finger 2000.

As shown in FIGS. 1, 2, and 6, and as described further herein, base 1200 can comprise one or more locking members and/or straps that can releasably, lockably lock at connection 5000. The location of connection 5000 may be chosen based on any of various factors. For example, as shown in FIGS. 1, 2, and 6, connection 5000 can be located substantially adjacent to lateral side 3400 and/or lateral side 3600 of arcuate toroidal member 1400 and/or anywhere along the locking members (not shown). Depending on how the locking members are implemented, connection 5000 might or might not create a flush environment facing surface in its vicinity on splint 1000.

Figure 5:
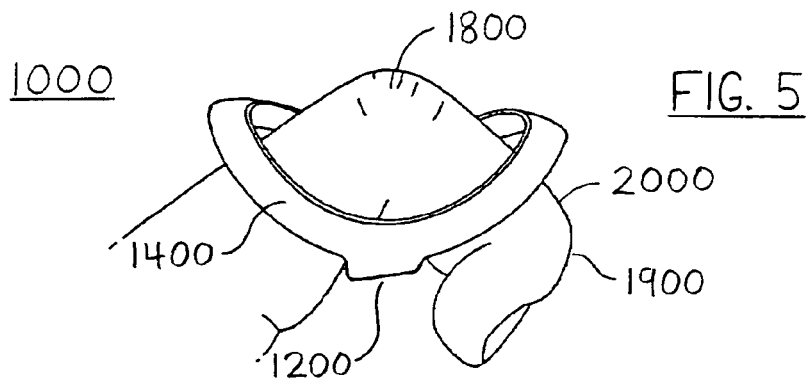
FIG. 5 is a side view of an exemplary embodiment of a finger splint 1000 in position on a flexed finger.

As shown in FIGS. 4 and 5, the base 1200 of splint 1000 can be positioned, when in use, on and/or substantially adjacent the volar surface 1600 of an interphalangeal joint 1800.

As shown in FIGS. 3 and 4, proximal semi-ellipsoidal portion 2800 and distal semi-ellipsoidal portion 3000 of splint 1000 can substantially lie in and/or intersect a first plane 3200, which can be substantially parallel or angularly inclined (not shown) with respect to the mid-longitudinal axis M-M of extended finger 2000. As measured from an approximate mid-point of intersection 3500, which can fall on a line K-K, which can lie in a plane that is perpendicular to all planes containing axis M-M, proximal semi-ellipsoidal portion 2800 can be longer than distal semi-ellipsoidal portion 3000 in a direction parallel to axis M-M. Alternatively (not shown), proximal semi-ellipsoidal portion 2800 can be of equal length to distal semi-ellipsoidal portion 3000 in a direction parallel to axis M-M.

With respect to line K-K, base 1200 of splint 1000 can form an angle X of from approximately 0 to approximately 20 degrees, including all values therebetween, such as for example, approximately 3.55, 6.2, 7, 8.5, 10, 12.33, 15, etc. degrees, and including all subranges therebetween. Thus, base 1200 can be angled with respect to a plane containing line K-K, that plane is perpendicular to all planes containing axis M-M.

As shown in FIGS. 4 and 6, arcuate toroidal member 1400 can conform to the dorsum 2200 of a finger 2000 and/or sides 3400 and 3600 can impinge at the axis of the joint of a finger such that the splint 1000 can provide lateral stability to a finger 2000 at the interphalangeal joint 1800 or 1900 of the finger 2000 and/or prevent migration of the splint 1000 on a finger 2000. Arcuate toroidal member 1400 can be in continuous contact with a finger 2000 when the finger 2000 is in a fully extended position.

Base 1200 can have a width sufficient to provide stability on the volar surface 16 of the interphalangeal joint 1800 and 1900 while allowing full flexion or bending of the PIP joint 1800 or DIP joint 1900 around the base 1200 towards the palmar surface 1600 of the hand of a user.

As shown in FIG. 4, splint 1000 can block the final degrees of extension of the PIP joint 1800 of a finger 2000. Arcuate toroidal member 1400 can distribute the pressure that occurs when there is a forceful extension bringing the finger 2000 into extension at the PIP joint 1800 or the DIP joint 1900 and/or can lessen the likelihood that a user will experience any discomfort from the splint 1000.

Figure 7:
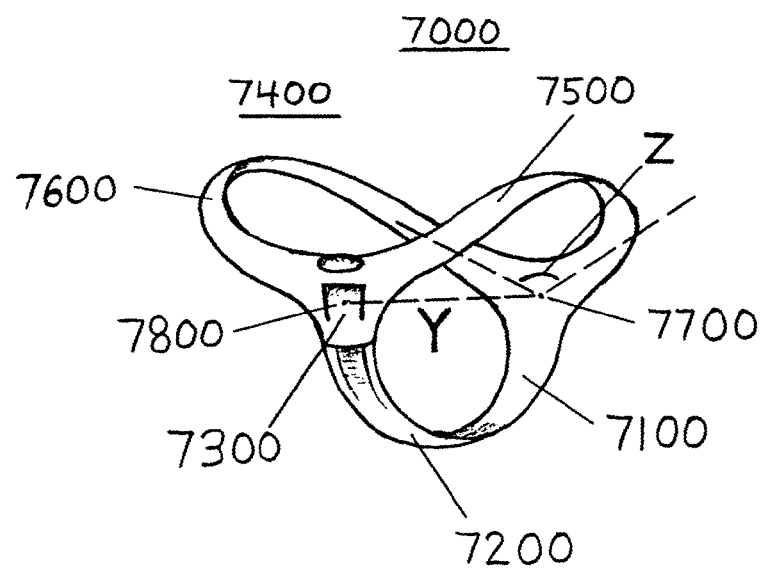
FIG. 7 is a perspective view of an exemplary embodiment of a system 7000.

FIG. 7 is a perspective view of an exemplary embodiment of an adjustable system, device, and/or splint 7000, which can comprise a base and/or an adjustable locking system 7100 that comprises a lockable strap 7200 that can adjustably connect to a releasable lock 7300 so that splint 7000 can be adjusted to fit any of a range of digit circumferences. Base 7100 can be formed integrally with arcuate member 7400, which can be comprised of an arcuate semi-elliptical portion 7500 and an arcuate semi-elliptical portion 7600, which can intersect at locations 7700 and 7800. Intersection 7700 and/or intersection 7800 can approximately define an angle Z, which can range from approximately 30 degrees to approximately 150 degrees, including all values therebetween, such as approximately 30, 45, 60.01, 75, 90, 99.2, 105, 120, and/or 135, etc. degrees, and all subranges therebetween. Intersections 7700 and 7800 can define therebetween a line Y, which can be approximately parallel to a major or minor axis of at least one of arcuate semi-elliptical portion 7500 and arcuate semi-elliptical portion 7600. As shown, intersections 7700 and 7800 can lie, and/or be adapted to lie, on opposing sides of the splinted digit. As shown in FIGS. 1-6, such intersections can lie, and/or be adapted to lie, below a dorsal surface and/or a longitudinal axis of the splinted digit, and/or above a volar surface of the splinted digit.

Figure 8:
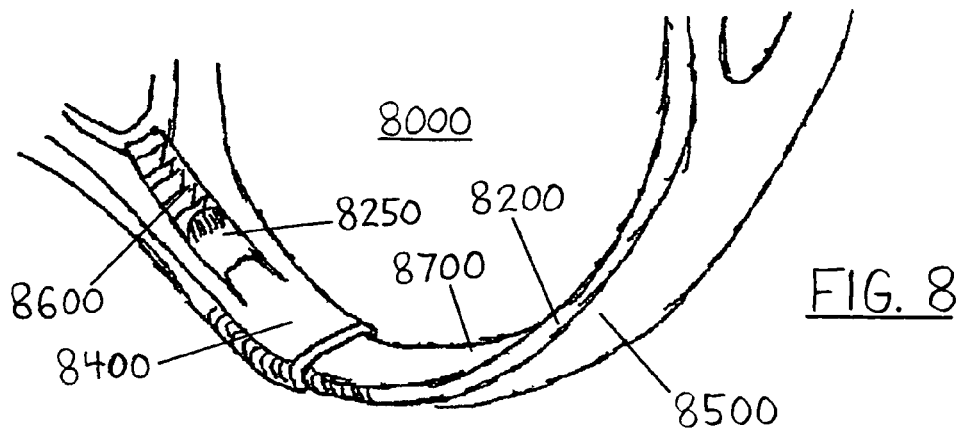
FIG. 8 is a perspective view of an exemplary embodiment of a system 8000 in an closed configuration.

FIG. 8 is a perspective view of an exemplary embodiment of an adjustable locking system 8000 for a splint, the adjustable locking portion shown in a closed configuration. System 8000 can comprise a lockable member 8200, which can be configured as a first strap, which can adjustably connect to a releasable lock 8400, which can be configured as a second strap, via an engagement end 8250 of member 8200 engaging with one or more transverse locking teeth 8600 of lock 8400. As shown, when engaged, lockable member 8200 and releasable lock 8400 can present a substantially uniformly flush environment facing surface 8500 and/or a substantially uniformly flush skin-facing surface 8700.

Figure 9:
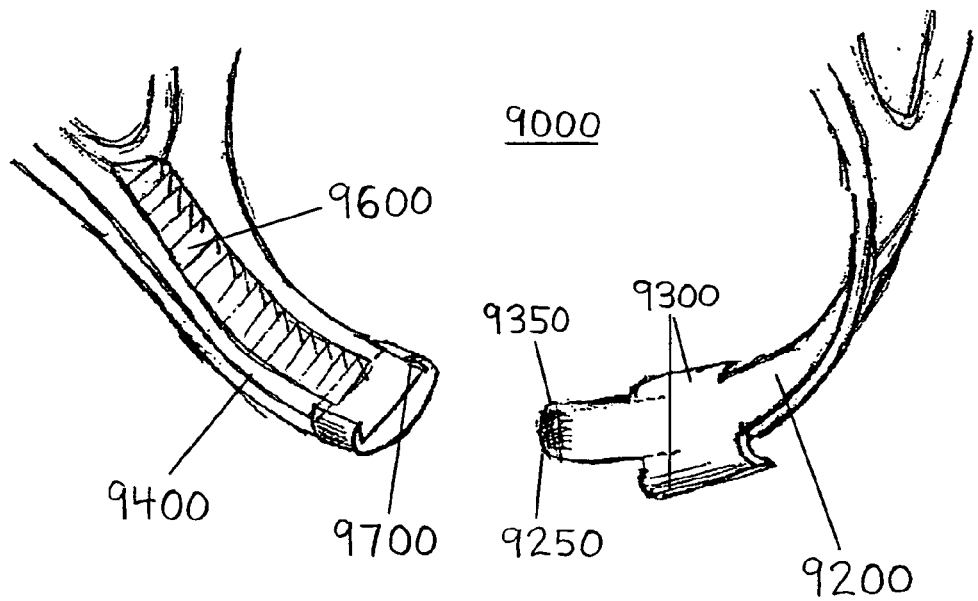
FIG. 9 is a perspective view of an exemplary embodiment of a system 9000 in an open configuration.

FIG. 9 is a perspective view of an exemplary embodiment of an adjustable locking system 9000 for a splint, the adjustable locking portion shown in an open configuration. System 9000 can comprise a lockable member 9200, which can be configured as a strap. Lockable member 9200 can adjustably connect to a releasable locking member 9400, which can be configured as a strap, via an engagement end 9250 of member 9200 engaging with one or more engagement teeth 9600 of lock 9400. Wings 9300 can assist with alignment and/or securement of straps 9200 and 9400. Channel 9700, which can have a cross-sectional shape (such as a substantially dovetail cross-sectional shape) for receiving a corresponding cross-sectional shape of lockable member 9200, can assist with alignment and/or securement of straps 9200 and 9400. At approximately end 9250 of member 9200 can be a tab and/or ridge 9350 for permitting ease of manipulation of member 9200.

Figure 10:
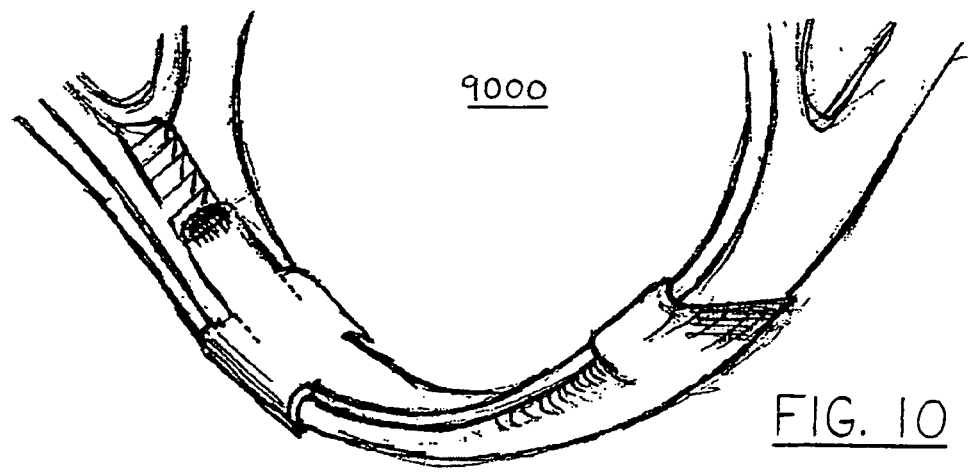
FIG. 10 is a perspective view of an exemplary embodiment of a system 9000 in a closed configuration.

FIG. 10 is a perspective view of an exemplary embodiment of FIG. 9's adjustable locking system 9000 for a splint, the adjustable locking portion shown in a closed configuration.

Figure 11:
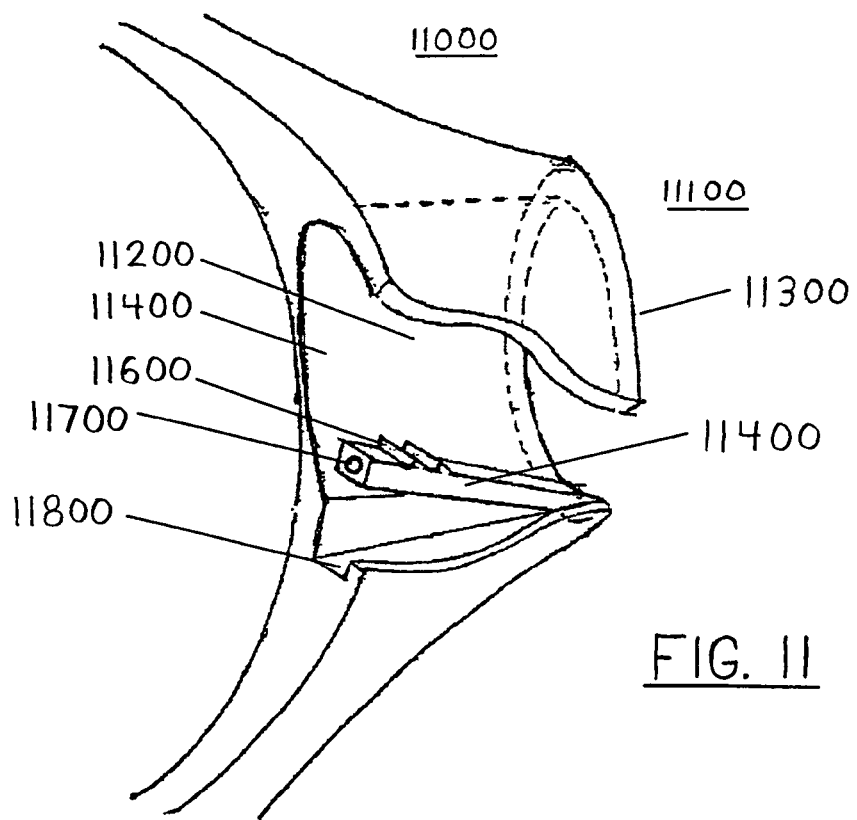
FIG. 11 is a perspective cut-away view of an exemplary embodiment of a system 11000.

FIG. 11 is a perspective cut-away view of an exemplary embodiment of a releasable locking member 11000, which can define a pull-through opening 11100 for receiving a corresponding strap and/or locking member. Releasable locking member 11000 and/or pull-through opening 11100 can define a passageway 11200 that spans between in ingress 11300 and an egress 11400. Releasable locking member 11000 and/or pull-through opening 11100 can comprise a spring-loaded and/or biased tooth bar 11500 that comprises a plurality of teeth 11600. Tooth bar 11500 can comprise a release mechanism 11700, such as an aperture into which a paper clip, pen, pin, etc., can be inserted to urge tooth bar 11500 in a rotational and/or deflectional direction opposite the direction of bias and into channel 11800, thereby disengaging the teeth 11600 of tooth bar 11500 from the corresponding teeth and/or ridges of the strap and/or locking member (not shown) to which locking member 11000 is releasably lockably engaged.

Figure 12:
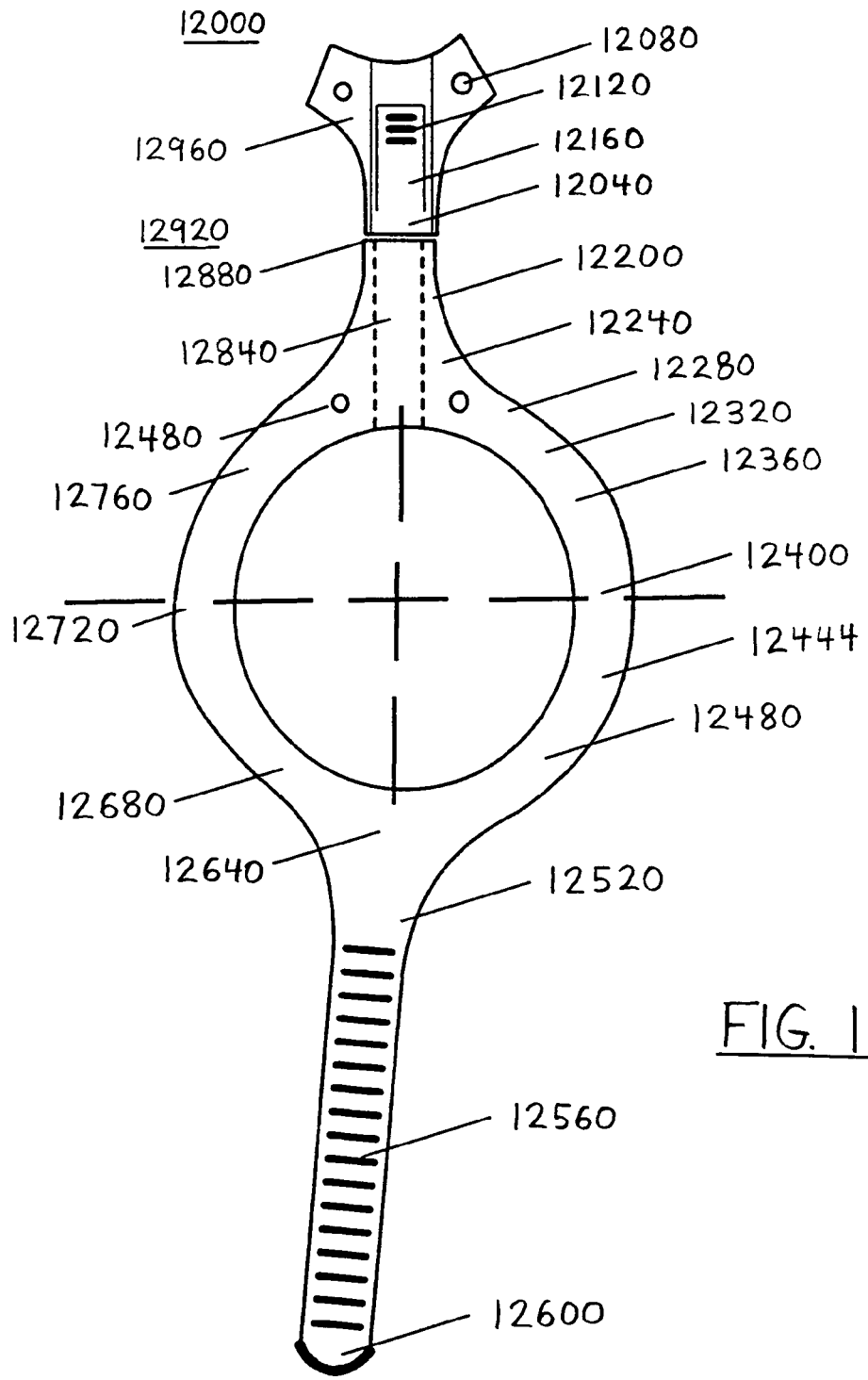
FIG. 12 is a top view of an exemplary embodiment of a system 12000.

FIG. 12 is a top planar view, flat, as molded, and prior to forming into a splint shape, of an exemplary embodiment of an adjustable system 12000, which can serve as a digit splint. Splint 12000 can be formed into an arcuate annular body and/or a unitary semi-rigid arcuate toroidal member 12320, which can comprise ring portions or arcuate semi-elliptical portions 12360 and 12680. In various embodiments, first arcuate semi-elliptical portion 12360 can be considered to extend from approximately location 12240 to approximately location 12640 (and thus include sub-portions 12280 and 12480) and second arcuate semi-elliptical portion 12760 can be considered to extend from approximately location 12640 to location 12240 (and thus include sub-portions 12700 and 12760). In either event, first arcuate semi-elliptical portion 12360 can be coupled to a second ring portion or a second arcuate semi-elliptical portion 12680.

Intersecting, at location 12640, and formed integral to body or member 12320 can be a first locking member and/or strap 12520, which can comprise one or more locking means 12560, such as one or more teeth, ridges, posts, detents, bumps, apertures, slots, grooves, notches, buckles, snaps, hooks, and/or loops, etc., which can be located on and/or at a major surface 12440 of splint 12000. An end 12600 of strap 12520 can be adapted to be received by a second locking member and/or strap 12920, which can be formed by combining and/or overlapping cover 12960 with base 12200, either of which can comprise one or more locking means 12120, such as one or more teeth, ridges, posts, detents, bumps, apertures, slots, grooves, notches, buckles, snaps, hooks, and/or loops, etc.

Although for ease of initial manufacturing (e.g., injection molding), cover 12960 can be initially formed in the shown location and orientation, cover 12960 can be detached from one or more attachment points to end 12880 of base 12200, flipped approximately 180 degrees within its plane, and coupled to base 12200. This coupling can occur via mating posts 12080 with apertures 12800 and/or via mating locking bar 12160 with groove 12840, such that end 12040 approximately overlaps end 12880 and posts (or apertures) 12080 overlap and engage with apertures (or posts) 12800. Thus, end 12600 of strap 12520 can be received into second locking member and/or strap 12920 at approximately overlapping ends 12880 and 12040, and locking means 12120 can releasably lockable engage with locking means 12560.

For adjustability, locking means 12560 can comprise a series of teeth, ridges, posts, etc., that can be spaced approximately 0.5 to approximately 2.5 millimeters apart (including all values and subranges therebetween) to correspond to the approximate desired circumferential increments of splint 12000. For example, the spacing can be approximately 1.25 millimeters, which can correspond to approximately 0.4 millimeters diameter increments, which approximately corresponds to the increments between jewelers half ring sizes. In certain exemplary embodiments, locking means 12560 and locking means 12120 can cooperate to allow for substantially continuously adjustable (i.e., not substantially incremented) changes in the circumference of splint 12000. This can be accomplished by using, for example, a clamp, a hook-and-loop fastener mechanism, and/or a releasable, reusable adhesive approach.

Figure 13:
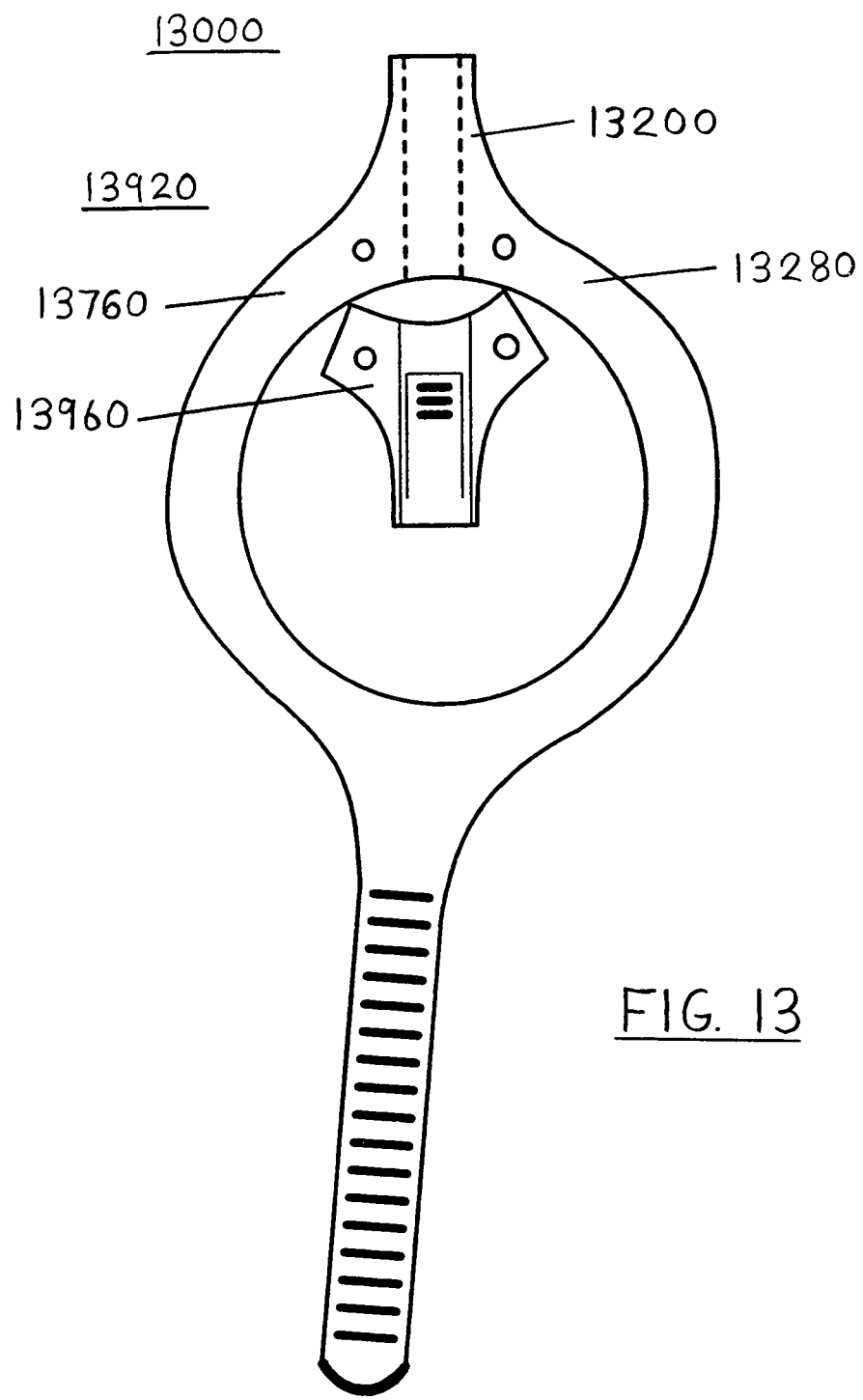
FIG. 13 is a top view of an exemplary embodiment of a system 13000.

FIG. 13 is a top planar view of an exemplary embodiment of a system 13000, which can serve as a digit splint. Although in this embodiment, in contrast to system 12000 of FIG. 12, cover 13960 can be initially formed in the shown location and orientation, cover 13960 can be detached from one or more attachment points to sub-portions 13760 and/or 13280, flipped approximately 180 degrees within its plane, and coupled to base 13200, such as in the manner described for system 12000.

Figure 14:
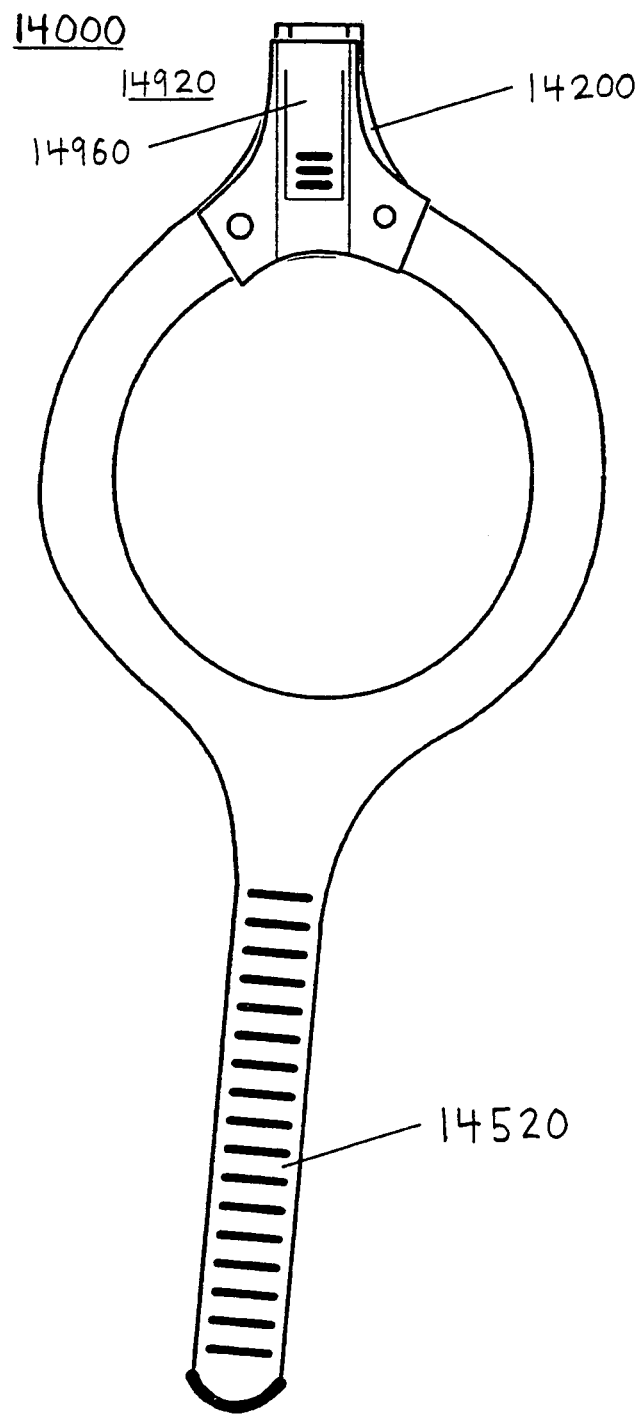
FIG. 14 is a top view of an exemplary embodiment of a system 14000.

FIG. 14 is a top planar view of an exemplary embodiment of a system 14000, which can serve as a digit splint. Second locking member and/or strap 14920 is shown ready for engagement with first locking member and/or strap 14520, in which cover 14960 overlaps and/or covers base 14200.

Figure 15:
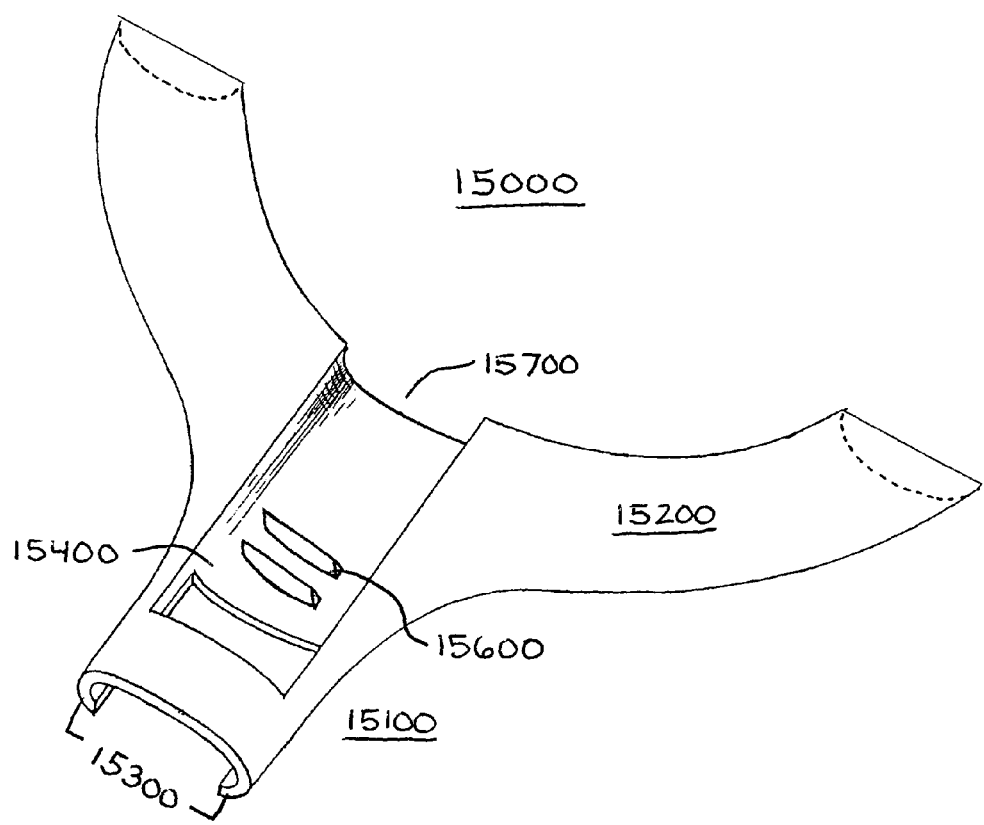
FIG. 15 is a perspective view of an exemplary embodiment of a system 15000.

FIG. 15 is a perspective view of an exemplary embodiment of a system 15000, which can comprise a releasable locking member 15100 formed integrally with and/or intersecting an arcuate toroidal member 15200. In certain embodiments, releasable locking member 15100 can be similar to releasable locking member 9400 of FIG. 9. Releasable locking member 15100 can comprise securement wings 15300 adapted to align a corresponding locking member (such as a strap-like member) (not shown) with a receiving channel and/or groove 15400. Releasable locking member 15100 can comprise a plurality of grooves and/or teeth 15600 to grip and/or secure the corresponding locking member. Releasable locking member 15100 can comprise an access aperture 15700 to allow access to the corresponding locking member to allow releasing a connection between locking member 15100 and the corresponding locking member (not shown).

The adjustable splints disclosed herein can be manufactured from a light-weight, temperature-resistant, and/or water-resistant material, such as semi-flexible plastic and/or resin of sufficient rigidity. Suitable materials can comprise polypropylene and/or polyethylene.

The material can be clear, translucent, opaque, and/or pigmented to provide a skin tone color. A skin tone color material can be aesthetically attractive and/or of low visibility so that a user may wear one or more adjustable splints without drawing attention to the hands or fingers of the user. The surface texture of the material can be sufficiently smooth to avoid skin irritation of the digit to which the splint is applied and/or adjacent digits, and/or to avoid snagging and/or abrading clothing, hair, etc.

A method of manufacturing adjustable splints can generally comprise: molding the splint as a continuous planar and/or arcuate form without palpable seams from a light-weight, temperature-resistant, and/or water-resistant material and/or forming the splint into a desired arcuate shape. Adjustable splints can be molded utilizing an injection molding process in a multi-cavity mold. The mold can be made of metal such as stainless steel or aluminum.

By choosing a suitable material and/or by adjusting their circumference, adjustable splints can comfortable for a user to wear in some and/or all weather conditions. The locking straps molded as an integral part of adjustable splints can allow the splint to be adjustably sized to conform to a range of jeweler's standard ring sizes, which are well known to one of ordinary skill in the jewelry industry.

Adjustable splints can be molded in 2 to 6 splint lengths. Each such splint can have adjustable lockable straps having a range covering at least 2, 3, 4, 5, and/or 6 full ring sizes and/or at least 4, 6, 8, 10, and/or 12 half ring sizes. The ranges of sizes can be provided for the convenience of a user so that the user can choose a circumference that offers the greatest support and/or comfort. Adjustable splints can allow the user to custom size the splint to very nearly precisely the circumference desired by the user for an individual custom fit.

Molding an adjustable splint as a continuous form without palpable seams from the lightweight, temperature-resistant, and/or water-resistant material can provide a durable lightweight splint which can be minimally invasive. The user can wear as many splints as necessary and/or desired, to inhibit hyperextension and/or provide lateral stability to the affected digits such as fingers, thumbs, and/or toes.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, such as via an explicit definition, there is no requirement for the inclusion in any claim herein (or of any claim of any application claiming priority hereto) of any particular described or illustrated characteristic, function, activity, or element, any particular sequence of activities, or any particular interrelationship of elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all subranges therein. Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A splint for a predetermined digit of a human body comprising:
    an arcuate annular body comprising a first arcuate semi-elliptical portion integrally formed with and coupled to a second arcuate semi-elliptical portion;
    a first strap integrally formed with and coupled to said body, said first strap comprising a first locking member and comprising a first major surface adapted to be disposed toward said predetermined digit;
    a second strap integrally formed with said body, said second strap comprising a second locking member; and
    said first locking member of said first strap adapted to releasably lockably engage with said second locking member of said second strap;
    said splint adapted to allow a full, normal range of motion, and to block hyperextension or hyperflexion, of a corresponding digit of a normal human body; and
    when operatively coupled, a longitudinal axis defined by said first strap and said second strap is angled, and non-parallel, with respect to a plane perpendicular to all planes containing a longitudinal axis of the finger.

2. The splint of claim 1, wherein said first arcuate semi-elliptical portion and said second arcuate semi-elliptical portion are of a substantially similar size.

3. The splint of claim 1, wherein said first arcuate semi-elliptical portion is sized larger than said second arcuate semi-elliptical portion.

4. The splint of claim 1, wherein said first major surface of said first strap comprises a plurality of locking teeth thereon.

5. The splint of claim 1, wherein said first major surface of said first strap comprises a plurality of transverse locking teeth thereon.

6. The splint of claim 1, wherein said second locking member is formed integrally with said second strap.

7. The splint of claim 1, wherein said second locking member and said second strap are two separable pieces.

8. The splint of claim 1, wherein said second locking member is slideably mounted on said second strap.

9. The splint of claim 1, wherein said second locking member is deflectable.

10. The splint of claim 1, wherein said second locking member comprises locking teeth adapted to lockably engage with a plurality of transverse locking teeth of said first locking member of said first strap.

11. The splint of claim 1, wherein said first major surface of said first strap comprises a channel along at least a portion of a length of said first strap.

12. The splint of claim 1, wherein said first major surface of said first strap comprises a channel along at least a portion of a length of said first strap, said channel defining a substantially dovetail shape and said second strap engageable in said channel.

13. The splint of claim 1, wherein said first arcuate semi-elliptical portion intersects said arcuate second semi-elliptical portion.

14. The splint of claim 1, wherein said first arcuate semi-elliptical portion intersects said second arcuate semi-elliptical portion at an angle greater than 30 degrees.

15. The splint of claim 1, wherein said first arcuate semi-elliptical portion intersects said second arcuate semi-elliptical portion at an angle less than 150 degrees.

16. The splint of claim 1, wherein an pair of intersections of said first arcuate semi-elliptical portion with said second arcuate semi-elliptical portion defines a line.

17. The splint of claim 1, wherein said first arcuate semi-elliptical portion intersects said second arcuate semi-elliptical portion at a pair of intersections connectable by a line parallel to a minor axis of at least one of said arcuate semi-elliptical portions.

18. The splint of claim 1, wherein said first arcuate semi-elliptical portion intersects said second arcuate semi-elliptical portion at a pair of intersections adapted to be positioned on opposing sides of the predetermined digit.

19. The splint of claim 1, wherein said first arcuate semi-elliptical portion intersects said second arcuate semi-elliptical portion at a pair of opposing intersections adapted to be positioned below a dorsal surface of the predetermined digit.

20. The splint of claim 1, wherein said first arcuate semi-elliptical portion intersects said second arcuate semi-elliptical portion at a pair of opposing intersections adapted to be positioned above a volar surface of the predetermined digit.

21. The splint of claim 1, wherein said first strap has a pull-through opening thereon having an ingress, an egress, and an internal passageway communicating therebetween.

22. A splint, comprising:
a unitary semi-rigid arcuate toroidal member;
a first lock portion integral to and extending from a first location on said arcuate toroidal member;
a second lock portion integral to and extending from a second location on said arcuate toroidal member, said first lock portion adapted to releasably lockably engage said second lock portion so as to allow for adjustable contact of at least a portion of said arcuate toroidal member with a predetermined portion of a body of a wearer of said splint, wherein, when operatively coupled, a longitudinal axis defined by said first lock portion and said second lock portion is angled, and non-parallel, with respect to a plane perpendicular to all planes containing a longitudinal axis of the predetermined portion of said body of said wearer;
said splint adapted to allow a full, normal range of motion, and to block hyperextension or hyperflexion, of a corresponding portion of a normal human body.

23. A splint, comprising:
a unitary semi-rigid member comprising:
a first ring portion and a second ring portion, each of said ring portions formed into a substantially arcuate semi-elliptical shape;
a first strap portion extending from said first ring portion;
a second strap portion extending from said second ring portion;
said first strap portion adapted to releasably lockably engage said second strap portion so as to allow for adjustable engagement of said ring portions with a predetermined portion of a wearer's body, wherein, when operatively coupled, a longitudinal axis defined by said first strap portion and said second strap portion is angled, and non-parallel, with respect to a plane perpendicular to all planes containing a longitudinal axis of the predetermined portion of said wearer's body;
said splint adapted to allow a full, normal range of motion, and to block hyperextension or hyperflexion, of a corresponding portion of a normal human body.

24. The splint of claim 23, wherein said second strap portion defines a channel for receiving said first strap portion.

25. The splint of claim 23, wherein said first strap portion comprises a plurality of locking teeth, and wherein said second strap portion comprises a plurality of mating teeth mateable with said locking teeth.

26. The splint of claim 23, wherein said first strap portion comprises a plurality of locking teeth spaced equidistantly by half ring sizes.

27. The splint of claim 23, wherein said first strap portion and said second strap portion provide a substantially uniformly flush environment facing surface when engaged.

28. The splint of claim 23, wherein said first strap comprises a tab portion at an end thereof for permitting ease of manipulation of said first strap portion.

29. A splint, comprising:
a unitary support member comprising at least two ring portions, said ring portions being substantially arcuate semi-elliptical in shape and comprising respective first and second end points which intersect at respective first and second intersection points,
a first strap member secured to and extending from said support member at said first intersection point, and
a second strap member secured to and extending from said support member at said second intersection point, said second strap member further being adapted for removable engagement to said first strap member, wherein a longitudinal axis defined by said first strap member and said second strap member is angled, and non-parallel, with respect to a plane perpendicular to all planes containing a longitudinal axis of a predetermined part of a wearer's body to which said splint is operatively attached;
said splint adapted to allow a full, normal range of motion, and to block hyperextension or hyperflexion, of a corresponding part of a normal human body.

30. The splint of claim 29, wherein said corresponding part is a digit.

* * * * *